United States Patent
Yi et al.

(10) Patent No.: US 8,574,147 B2
(45) Date of Patent: Nov. 5, 2013

(54) PRESSURE-TO-TENSION CONVERSION DEVICE FOR TREATING URINARY INCONTINENCE

(76) Inventors: Jeong Yoon Yi, Daejeon (KR); Hwa Jeong Yi, Daejeon (KR); Su Ho Yi, Daejeon (KR)

( * ) Notice: Subject to any disclaimer, the term of this patent is extended or adjusted under 35 U.S.C. 154(b) by 473 days.

(21) Appl. No.: 12/857,244

(22) Filed: Aug. 16, 2010

(65) Prior Publication Data

US 2011/0004049 A1    Jan. 6, 2011

Related U.S. Application Data

(63) Continuation of application No. PCT/KR2009/005549, filed on Sep. 29, 2009.

(30) Foreign Application Priority Data

Jul. 2, 2009    (KR) .................... 10-2009-0060210

(51) Int. Cl.
*A61F 2/00*    (2006.01)

(52) U.S. Cl.
USPC .......................................................... 600/30

(58) Field of Classification Search
USPC .................... 600/29–31, 37; 606/151–158
See application file for complete search history.

(56) References Cited

U.S. PATENT DOCUMENTS

| | | | |
|---|---|---|---|
| 5,123,428 A | 6/1992 | Schwarz | |
| 6,808,485 B2 | 10/2004 | Zunker | |
| 2003/0062052 A1 | 4/2003 | Carter et al. | |
| 2005/0261547 A1* | 11/2005 | Bouffier | 600/37 |
| 2009/0082617 A1* | 3/2009 | Vecchiotti et al. | 600/30 |

FOREIGN PATENT DOCUMENTS

| | | |
|---|---|---|
| EP | 0826381 A2 | 3/1998 |
| JP | 6501627 | 2/1994 |
| JP | 10155897 | 6/1998 |
| WO | 9206652 | 4/1992 |
| WO | 9620749 | 7/1996 |
| WO | 0226173 A2 | 4/2002 |
| WO | 2006015042 A1 | 2/2006 |
| WO | 2006119273 A2 | 11/2006 |
| WO | 2009023256 A2 | 2/2009 |
| WO | 2011002131 A1 | 1/2011 |

OTHER PUBLICATIONS

Official Notice of Preliminary Rejection Japanese Patent Application No. 2011-521057, dated Jul. 17, 2012, 3 pages.

* cited by examiner

*Primary Examiner* — Charles A Marmor, II
*Assistant Examiner* — Catherine E Burk
(74) *Attorney, Agent, or Firm* — Rothwell, Figg, Ernst & Manbeck, P.C.

(57) ABSTRACT

Disclosed is a pressure-to-tension conversion device for treating urinary incontinence. The pressure-to-tension conversion device includes resilient sections which are inserted in and occupy Retzius spaces positioned in left and right sides of the urethra in front of the urinary bladder, respectively, and a support extending below the urethra and across the resilient sections in a "V" shape, wherein if the resilient sections are deformed as the abdominal pressure increases and the Retzius spaces contract, the support is tensioned, thereby supporting the urethra, so that the urinary incontinence can be treated. Consequently, the length of operation time for transplanting the pressure-to-tension conversion device can be shortened, a complication or a side effect can be reduced, and the charges of operation can be reduced. In addition, expensive operation materials can be substituted by the pressure-to-tension conversion apparatus, the costs for operation materials can be saved.

2 Claims, 4 Drawing Sheets

PRESSURE-TO-TENSION CONVERSION DEVICE FOR TREATING URINARY INCONTINENCE

CROSS REFERENCE TO RELATED APPLICATIONS

The present application claims priority to International Application PCT/KR2009/005549, with an international filing date of Sep. 29, 2009, which claims the benefit of Korean Patent Application No. 10-2009-0060210 filed in the Korean Intellectual Property Office on Jul. 2, 2009, which is incorporated herein in its entirety.

TECHNICAL FIELD

The present invention relates to a pressure-to-tension conversion device for treating urinary incontinence, and more particularly to a pressure-to-tension conversion device for treating urinary incontinence which can be positioned in Retzius spaces after minimally cutting open only the suburethra, so that pressure, which is applied to the pressure-to-tension conversion device due to the increase of pressure around the Retzius spaces, i.e. due to the increase of abdominal pressure, increases the pressure applied to the suburethra, whereby substantial effects for treating urinary incontinence can be obtained.

BACKGROUND ART

Urinary incontinence is an unintentional urine discharge symptom. The urinary incontinence symptom occurs when abdominal pressure increases due to physical exercise, moving, laughing or coughing. The urinary incontinence may be caused by the increase of age, pregnancy, birth, chronic cough, excessive exercise, or the like, and may get worse due to fatness or menopause. Such urinary incontinence symptom usually occurs when urethral sphincters for supporting the urethra and the urinary bladder are weakened.

Various technologies for treating such urinary incontinence are disclosed in a plurality of documents, including U.S. Pat. No. 6,808,485, Japanese Unexamined Patent Publication No. 1998-155897, and Korean Unexamined Patent Publication No. 2003-34218, which propose to insert an elastic insert in the virginal canal, or to inject hydrogel particles (polymer) into tissues around the urethra or the ureter.

Recently, the urinary incontinence is treated by supporting the suburethra (the bottom area of the urethra), wherein the suburethra is supported by forming a passage through the suburethra from an inguinal region using a guide needle holder, and then hanging the guide needle holder on a prolene mesh (or in the reversed sequence).

However, the recent urinary incontinence treatment process typically requires spinal anesthesia or sleep anesthesia, although the treatment process is the minimal invasive surgery process among the existing ones, and may cause the damage of muscles, ligaments, and blood vessels in the route: the inguinal region→the obturator foramen→the suburethra. Due to this reason, the possibility of damaging other anatomical structures or propagating inflammation is very high. In addition, a device causing damage, e.g. a guide needle holder, is needed.

DISCLOSURE

Technical Problem

Accordingly, the present invention has been made to solve the above-mentioned problems in the prior art, and the present invention provides a pressure-to-tension conversion device for treating urinary incontinence which can be positioned in Retzius spaces after minimally cutting open only the bottom area of the urethra, so that pressure, which is applied to the pressure-to-tension conversion device due to the increase of abdominal pressure, increases the pressure applied to the bottom area of the urethra, whereby substantial effects for treating urinary incontinence can be obtained.

Technical Solution

In accordance with an aspect of the present invention, there is provided a pressure-to-tension conversion device for treating urinary incontinence, the pressure-to-tension conversion device including: resilient sections which are inserted in and occupy Retzius spaces positioned in left and right sides of the urethra in front of the urinary bladder, respectively; and a support provided below the urethra to extend across the resilient sections in a "V" shape, whereby if the resilient sections are deformed when the abdominal pressure increases and the Retzius spaces contract, the support is tensioned to such an extent that it can support the urethra so as to treat the urinary incontinence.

Preferably, the support takes a form of a string, and extends across the resilient sections by being fixed through the first resilient sections at the opposite ends thereof in such a manner that the opposite ends cannot be released from the first resilient sections, whereby if the resilient sections are broadened thinly due to the abdominal pressure, the support is tensioned to such an extent that it can support the urethra.

In addition, the resilient sections and the support preferably take a form of a bag filled with a fluid substance, whereby if the resilient sections are deformed due to the abdominal pressure, the fluid substance flows into and inflates a feature of the support confronting the urethra to such an extent that the support is tensioned and supports the urethra.

Moreover, the resilient sections are preferably returned to their original shapes due to the resiliency thereof if the abdominal pressure is released.

Advantageous Effects

Since the operation for transplanting the inventive pressure-to-tension conversion device does not require a guide needle holder, and is minimally invasive, it is possible to significantly reduce damage associated with a conventional invasive operation.

In addition, the operation for transplanting the inventive pressure-to-tension conversion device does not require spinal anesthesia nor sleep anesthesia at all, and does not cause any inconvenience that may be caused when an operation is performed with unreasonable local anesthesia.

In addition, if the treatment effect is insufficient, the inventive pressure-to-tension conversion device can be easily additionally calibrated through a non-invasive process.

Moreover, since the inventive pressure-to-tension conversion device can be easily removed, it is easy to perform re-operation in another way if the pressure-to-tension conversion device is not efficient for treatment.

Consequently, the time required for the transplanting operation can be shortened, a complication or a side effect caused by the operation can be reduced, and the charges of operation can be reduced. In addition, expensive operation materials can be substituted by the inventive pressure-to-tension conversion device, the costs for operation materials can be saved.

EXPLANATION OF SYMBOLS FOR THE MAJOR PARTS OF THE DRAWINGS

| | |
|---|---|
| 10: | first resilient section |
| 20: | first support |
| 21: | end |
| 25: | stopper |
| 101: | urinary bladder |
| 103: | urethra |
| 105: | Retzius space |
| 210: | second resilient section |
| 220: | second support |
| 221: | feature |
| 223: | flexible tube part |
| 230: | fluid substance |

Best Mode

Mode for Invention

Hereinafter, exemplary embodiments of the present invention will be described with reference to the accompanying drawings.

Figure 1:
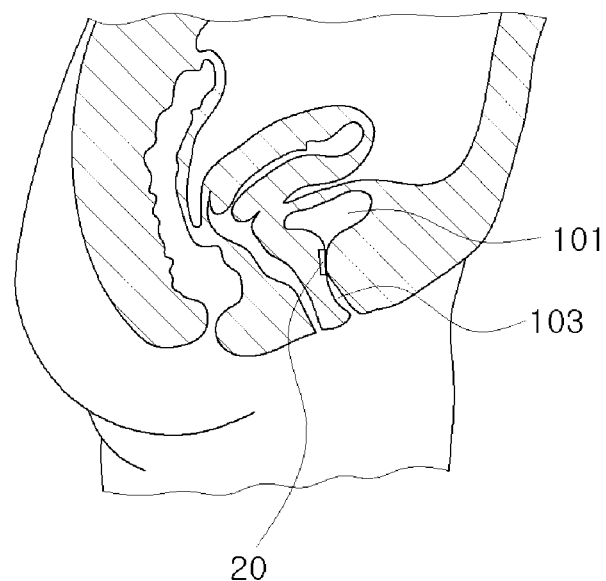
FIGS. 1 and 2 show a pressure-to-tension conversion device for treating urinary incontinence in accordance with a first embodiment of the present invention in the transplanted state.
Figure 2:
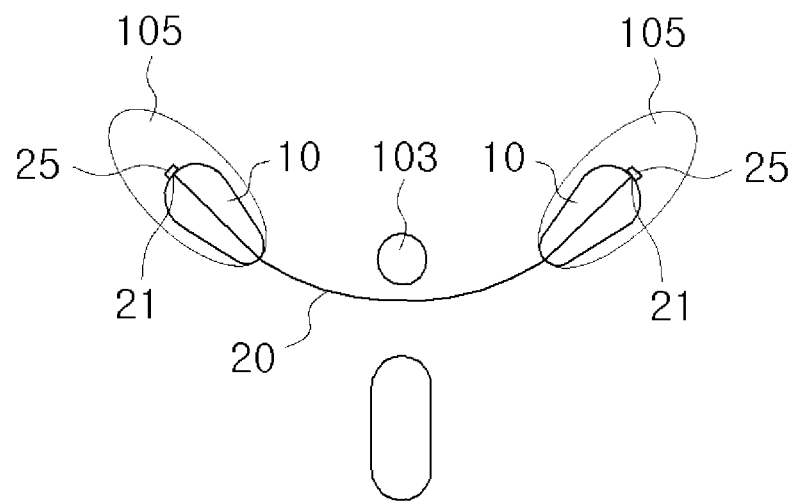
Figure 3:
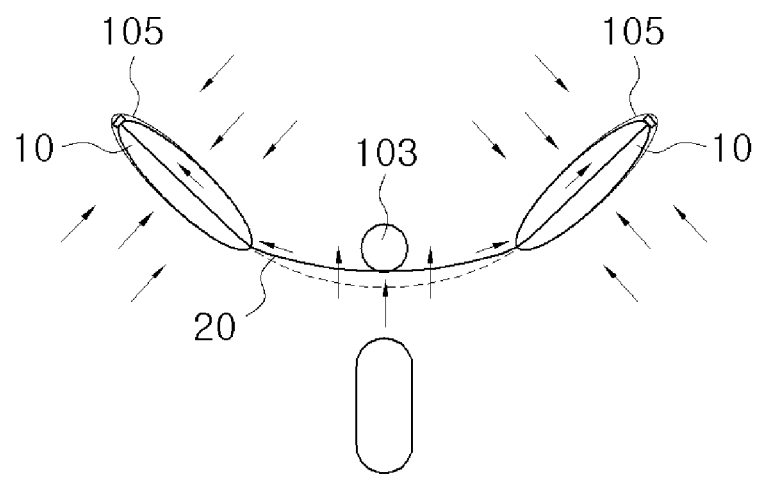
FIG. 3 shows the pressure-to-tension conversion device in accordance with the first embodiment of the present invention while it is being used.

FIGS. 1 and 2 show a pressure-to-tension conversion device for treating urinary incontinence in accordance with a first embodiment of the present invention in the transplanted state;

FIG. 3 shows the pressure-to-tension conversion device in accordance with the first embodiment of the present invention while it is being used;

As shown in the drawings, the pressure-to-tension conversion device for treating urinary incontinence treatment includes first resilient sections 10. The first resilient sections 10 are deformed when pressure is applied to the sections, and are returned to their original shapes due to their own resiliency when the pressure is released from the section. In addition, the first resilient sections are highly malleable.

That is, each of the first resilient sections 10 may have a well-known soft silicon bag like construction, which is broadened thinly when it is compressed, and is returned to its original shape when the pressure is released.

The first resilient sections 10 are inserted in and occupy Retzius spaces 105, respectively, wherein the Retzius spaces are positioned at left and right sides of the urethra 103 in front of the urinary bladder 101.

A first string-type support 20, such as a prolene mesh, is provided to extend across the first resilient sections 10 which are inserted in and occupy the Retzius spaces 105.

The first string-type support 20 has opposite ends 21, which are fixed through the first resilient sections 10 in such a manner that they cannot be released from the first resilient sections 10; thus, the first string-type support 20 extends across the first resilient sections 10. For example, the ends 21 are guided through and out of the first resilient sections 10, respectively, and stoppers 25 are fastened to the ends 21 of the support 20 so that the stoppers 25 prevent the ends 21 from being released from the first resilient sections 10, respectively. Here, since the first string-type support 20 is provided below the urethra 103 to extend across the first resilient sections 10, the first string-type support 20 takes a "V" shape as shown in FIG. 2.

Since the first embodiment of the present invention described above can be completely installed through a simple operation that minimally cuts open only the bottom area of the urethra 103, and then inserts the first resilient sections 10 in the Retzius spaces 105, respectively, a guide needle holder, which causes damage, is not required unlike the prior art. In addition, since the operation is minimally invasive, it is possible to significantly reduce damage associated with a conventional invasive operation.

In addition, the operation for the first embodiment does not require spinal anesthesia nor sleep anesthesia at all, and does not cause any inconvenience that may be caused when an operation is performed with unreasonable local anesthesia. In addition, if the operation is insufficient in terms of the treatment effect, the pressure-to-tension conversion device of the first embodiment can be easily additionally calibrated through a non-invasive process. Moreover, since the pressure-to-tension conversion device can be easily removed, it is easy to perform re-operation in another way if the pressure-to-tension conversion device is not efficient for treatment.

Therefore, if the Retzius spaces 105 contract due to the increase of abdominal pressure which is caused due to physical exercise, moving, laughing, or coughing, the first resilient sections 10 are broadened thinly and pull the first support 20. As a result, the first support 20 is tensioned and supports the urethra 103 to such an extent that the urethra 10 cannot be open, whereby urinary incontinence can be treated.

Then, if the abdominal pressure is released, the Retzius spaces 105 are returned to their original shapes. As a result, the first resilient sections 10 are also returned to their original shapes like the Retzius spaces 105, whereby the tension of first support 20 is released to its initial condition.

Figure 4:
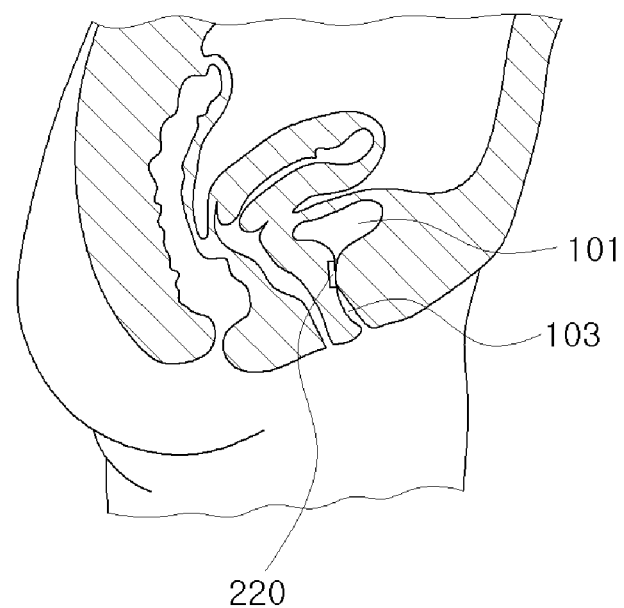
FIGS. 4 and 5 show a pressure-to-tension conversion device for treating urinary incontinence in accordance with a second embodiment of the present invention in the transplanted state.
Figure 5:
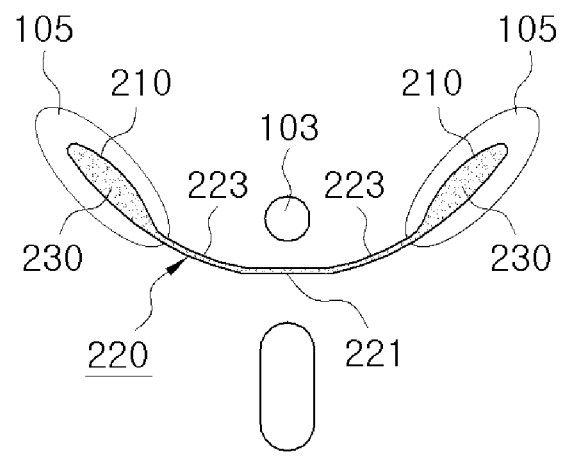
Figure 6:
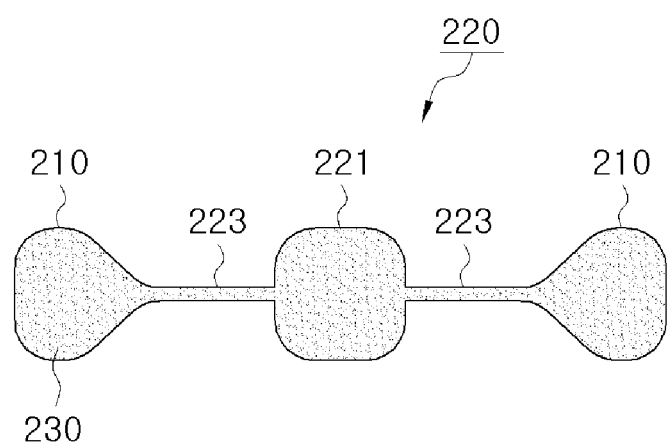
FIG. 6 shows the pressure-to-tension conversion device for treating urinary incontinence in accordance with the second embodiment of the present invention.

FIGS. 4 and 5 show a transplanted pressure-to-tension conversion device according to a second embodiment of the present invention. FIG. 6 shows a top plan view of the pressure-to-tension conversion device according to the second embodiment of the present invention.

Figure 7:
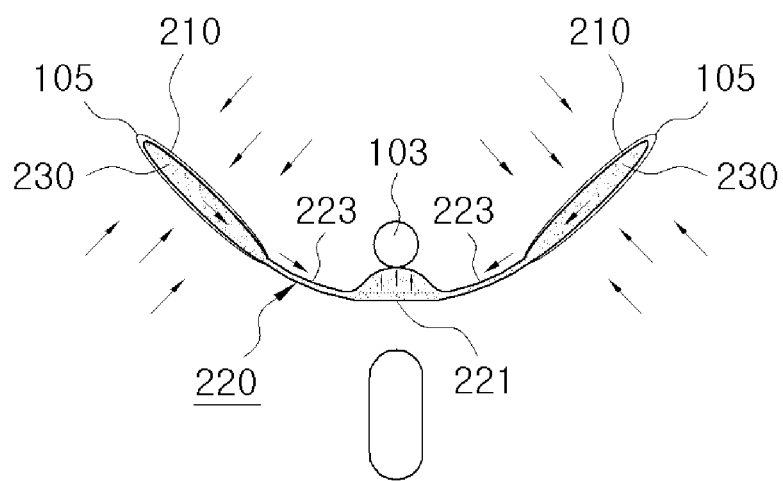
FIG. 7 shows the pressure-to-tension conversion device in accordance with the second embodiment of the present invention while it is being used.

FIG. 7 shows the pressure-to-tension conversion device according to the second embodiment of the present invention in the used state.

As shown in the drawings, the pressure-to-tension conversion device according to the second embodiment of the present invention includes second resilient sections 210 and a second support 220, which correspond to the first resilient sections 10 and the first support 20, respectively, wherein the second resilient sections 210 and the second support 220 take a form of a bag filled with a fluid substance 230, so that if the second resilient sections 210 are deformed due to the abdominal pressure, the fluid substance 230 flows to the feature 221 of the second support 220 confronting the urethra 103, thereby expanding or inflating the feature 221. As a result, the second support 220 is tensioned and supports the urethra 103, whereby the urinary incontinence can be treated.

That is, the second resilient sections 210 may take a shape of a soft silicon bag, which is filled with physiological salt solution as well-known in the art. In addition, in the second support 220, the feature 221 has the same construction as the second resilient sections 210, and flexible tube parts 223 extend from the feature 221 to the second resilient sections 210, respectively, so that the second support 220 can communicate with the second resilient sections 210. As a result, if the Retzius spaces 105 are contracted due to the increase of abdominal pressure and hence the second resilient sections 210 are pressed, as shown in FIG. 7, the fluid substance 230 in the second resilient sections 210 flows to the feature 221 thereby inflating the feature 221 so that the feature 221 supports the urethra 103 to such an extent that the urethra 10 cannot open, whereby urinary incontinence can be treated.

At this time, since the second resilient sections 210 are positioned within the normal Retzius spaces 105, they sense and transmit the increase of abdominal pressure to the second support 220 in real time without causing the anatomical deformation of the Retzius spaces 105. As shown in the drawing, since each of the second resilient sections 220 has a substantially longitudinally extending oval shape, it is possible to insert the second resilient sections 220 exposing the Retzius spaces 105 by exposing the Retzius spaces 105 by minimally cutting open the bottom area of the urethra 103, and the positional variation of the second resilient sections 220 in the Retzius spaces 105 can be controlled after they are inserted in the Retzius spaces 105.

In addition, since the second resilient sections 210 communicates with the tube parts 223, and the widths of the second resilient sections 210 are reduced as they approach the tube parts 223, the abdominal pressure sensed in real time can be readily directed to the tube parts 223.

The tube parts 223 of the second support 220 are formed from a very thin capillary tube, and transfer the fluid substance 230 in the second resilient sections 210 to the feature 221, thereby transferring the pressure from the second resilient sections 210 to the urethra 103. In addition, since the tube parts 223 are flexible, they can properly function along an "S" shaped anatomical structure formed from the bottom area of the urethra 103 to the Retzius spaces 105.

When the fluid substance 230 flows into the feature 221 of the second support 220 confronting the urethra 103, and hence the pressure is transferred to the feature 221, the feature 221 is inflated to such an extent that the feature 221 can support and press the urethra 103 with increased pressure. Consequently, the urinary incontinence can be treated.

The feature 221 of the second support 220 is curved so that it can smoothly wrap the bottom area of the urethra 103. As a result, the feature 221 does not causes the urethra 103 to be deformed, and allows pressure to be uniformly transferred to the entirety of the urethra 103 from the second resilient sections 210. If the pressure is released, the feature 221 is returned to its normal condition.

That is, if the abdominal pressure is removed, the first resilient sections 10 are also returned to their original shapes, and the fluid substance 230, which has flown into the feature 221 of the second support 220 due to the abdominal pressure, is returned to the first resilient sections 10. As a result, the feature 221 of the second support 220 is returned to its original condition.

The fluid substance 230 may be any of air, physiological salt solution, and cohesive gel.

Like the first embodiment described above, since the second embodiment of the present invention can be completely transplanted through a simple operation that minimally cuts open the bottom area of the urethra 103, and then inserts the first resilient sections 210 in the Retzius spaces 105, respectively, a guide needle holder, which causes damage, is not required unlike the prior art. In addition, since the operation is minimally invasive, it is possible to significantly reduce damage associated with a conventional invasive operation.

In addition, the operation for the first embodiment does not require spinal anesthesia nor sleep anesthesia at all, and does not cause any inconvenience that may be caused when an operation is performed with unreasonable local anesthesia. In addition, if the operation is insufficient in terms of the treatment effect, the pressure-to-tension conversion device of the first embodiment can be easily additionally calibrated through a non-invasive process. Moreover, since the pressure-to-tension conversion device can be easily removed, it is easy to perform re-operation in another way if the pressure-to-tension conversion device is not efficient for treatment.

Industrial Applicability

In accordance with the present invention, there is provided a pressure-to-tension conversion device which can exhibit substantial effects for treating urinary incontinence as described above.

The invention claimed is:

1. A pressure-to-tension conversion device for treating urinary incontinence, the pressure-to-tension conversion device comprising:
    resilient sections that are adapted to be inserted in and occupy Retzius spaces positioned in left and right sides of a urethra in front of a urinary bladder, respectively, wherein the resilient sections are composed of silicon and adapted to deform when an abdominal pressure increases; and
    a support adapted to be provided below the urethra to extend across the resilient sections and take on a "V" shape, whereby when the resilient sections are deformed when the abdominal pressure increases and the Retzius spaces contract, the support is tensioned to such an extent that it can support the urethra so as to treat the urinary incontinence,
    wherein the support takes a form of a string, and extends across the resilient sections by being fixed through the resilient sections at opposite ends thereof in such a manner that the opposite ends cannot be released from the resilient sections, whereby when the resilient sections are broadened thinly due to the abdominal pressure, the support is tensioned to such an extent that it can support the urethra.

2. The pressure-to-tension conversion device as claimed in claim 1, wherein the resilient sections are returned to their original shapes due to the resiliency thereof if the abdominal pressure is released.

* * * * *